(12) United States Patent
Niemann et al.

(10) Patent No.: US 7,275,418 B2
(45) Date of Patent: Oct. 2, 2007

(54) METHOD FOR THE QUANTITATIVE DETECTION OF TWO CONTAMINANTS IN A FLUID

(75) Inventors: Markus Niemann, Beckingen (DE); Monika Scherer, Bonn (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 11/376,807

(22) Filed: Mar. 15, 2006

(65) Prior Publication Data

US 2006/0207315 A1 Sep. 21, 2006

(30) Foreign Application Priority Data

Mar. 18, 2005 (DE) .................. 10 2005 012 452

(51) Int. Cl.
*G01N 15/00* (2006.01)
*G01N 33/26* (2006.01)

(52) U.S. Cl. .................. 73/53.07; 73/53.05; 73/10

(58) Field of Classification Search .............. 73/53.07, 73/53.05, 10

See application file for complete search history.

(56) References Cited

U.S. PATENT DOCUMENTS

| | | | | |
|---|---|---|---|---|
| 3,537,820 A | * | 11/1970 | Shah et al. | ................... 436/79 |
| 5,377,531 A | * | 1/1995 | Gomm | ...................... 73/53.05 |
| 5,750,887 A | * | 5/1998 | Schricker | ................... 73/117.3 |
| 5,754,055 A | * | 5/1998 | McAdoo et al. | ............ 324/636 |
| 6,253,601 B1 | * | 7/2001 | Wang et al. | ............... 73/117.3 |
| 6,286,363 B1 | * | 9/2001 | Discenzo | ................... 73/53.01 |
| 6,644,095 B2 | * | 11/2003 | Van Mullekom et al. | ....... 73/10 |
| 6,895,807 B2 | * | 5/2005 | Han et al. | .................. 73/53.05 |
| 2006/0118170 A1 | * | 6/2006 | Dykstra | ...................... 137/92 |

* cited by examiner

*Primary Examiner*—Michael Cygan
(74) *Attorney, Agent, or Firm*—Kenyon & Kenyon LLP

(57) ABSTRACT

The quantitative determination of two contaminants of a fluid is carried out in the following steps: detection of permittivity $\epsilon$ and viscosity v of the fluid; determination of the quantity of the first contaminant $11e$ on the basis of a difference between detected permittivity $\Delta\epsilon$ and a first preset value $10e$; estimation of viscosity $12n$ on the basis of the quantity of the first contaminant $11e$; and determination of the quantity of the second contaminant on the basis of a difference between detected viscosity v and estimated viscosity $12n$.

6 Claims, 1 Drawing Sheet

METHOD FOR THE QUANTITATIVE DETECTION OF TWO CONTAMINANTS IN A FLUID

BACKGROUND INFORMATION

Although the present invention is described below with reference to the determination of the soot and fuel concentrations in an aged motor oil, the present invention is not limited thereto, but rather generally relates to methods which use two physical variables to determine the quantity of two contaminants in a fluid. Motor oils are used in internal combustion engines to lubricate moving parts to reduce the friction and abrasion of metal surfaces moving relative to one another. Motor oil is subject to multiple aging processes which make it necessary to change the oil after a certain period of time. In this regard, it is extremely useful to provide a sensor device and a method which can detect the condition of the oil in an internal combustion engine during operation.

The condition of the motor oil is influenced in different ways by a wide range of aging processes. The effect of some aging processes on the properties and composition of the motor oil is known. Moreover, these aging processes may be identified by certain processes in an engine or equipment connected to the engine. Conversely, possible adjustment errors or defects in the motor or connected equipment may therefore be determined from the condition of the oil. This information is used in oil analyses which determine the composition of a used oil through complex physical-chemical laboratory process steps and, on the basis of this composition, enable conclusions to be drawn as to the condition of an engine. However, these oil analyses have the disadvantage that they cannot be carried out locally in a vehicle without a great deal of effort.

SUMMARY OF THE INVENTION

The method according to the present invention for the quantitative detection of two contaminants in a fluid involves the following steps: detection of two physical variables of the fluid, one physical variable being the viscosity and the second an electrical variable; determination of the quantity of the first contaminant on the basis of a difference between the detected physical variable and a first preset value; estimation of the second physical variable on the basis of the quantity of the first contaminant; and determination of the quantity of the second contaminant on the basis of a difference between the detected second variable and the estimated second physical variable.

An advantage of the present method is that two physical variables of the fluid are detectable in a vehicle during operation without requiring a great deal of measurement work. This also enables the condition of the motor oil to be monitored during vehicle operation.

According to a preferred embodiment, the electrical variable is the permittivity or specific resistance of the fluid.

According to an embodiment, fuel is determined as one contaminant and soot and/or oxidized components of the fluid as the other contaminant.

According to a further embodiment, the fluid includes oil.

According to a further embodiment, the quantity of the first and the second contaminants is determined by a first and a second linear dependency on the difference between the first and the second physical variable.

According to a further embodiment, the second physical variable is estimated via a third linear dependency on the quantity of the first contaminant.

According to a further embodiment, the first physical variable is determined for a fluid without using the first and the second contaminants as the preset value.

According to a further embodiment, the preset value and linear coefficients for the first, second and third linear dependencies are stored for different oil temperatures, and the temperature of the contaminated oil is determined.

DETAILED DESCRIPTION

Motor oils as well as other oils are used in a variety of ways to lubricate components moving relative to one other. These oils have a wide range of applications in internal combustion engines and transmissions. The physical-chemical properties of the oils change due to thermal and chemical influences. This "aging" of the oil usually increases the viscosity. If the viscosity exceeds a critical value, this may result in higher abrasion or, in the worst case, cause the piston to seize. If the viscosity drops below a critical value, this may result in the removal of the lubricating film between the moving parts, e.g., between the piston and the cylinder. It is therefore necessary to change the oil before this occurs. According to conventional methods, the oil is changed after a predetermined period of engine operation, e.g., vehicle mileage, or after a predetermined period of time. A sensor which detects the quality or condition of the motor oil may display a required early oil change or, if necessary, indicate that the oil is still in proper condition.

A wide range of processes influence the condition of the oil. When thermally activated, the motor oil oxidizes, particularly in the case of spark ignition engines. Oxidation produces aldehydes, ketones and carboxylic acids in the oil. Due to polymerization and polycondensation reactions, paint-, resin- and sludge-like deposits of a higher molecular weight which are largely oil-insoluble form from these starting materials. The oil-soluble aging products cause the oil viscosity to increase. In addition to oxidation, soot is the main cause of increased viscosity in diesel engines. This soot is produced in the form of an unwanted waste product during diesel combustion and enters into motor oil circulation in low concentrations. Exhaust treatment equipment causes a greater increase of soot in the oil, particularly if the soot-particulate filter is clogged and needs to be cleaned.

In internal combustion engines and, in particular, diesel engines, low concentrations of uncombusted fuel enter the motor oil. Because the oil and fuel mix well and the fuel also has a much lower viscosity than the oil, even low concentrations of fuel in the oil reduce the viscosity thereof.

Because the soot or oxidation and the fuel in the oil influence viscosity in such a way that they may at least partially compensate for each other, only a qualitative and uncertain statement on the condition of the oil is obtained by determining only the viscosity as a measure.

Figure 1:
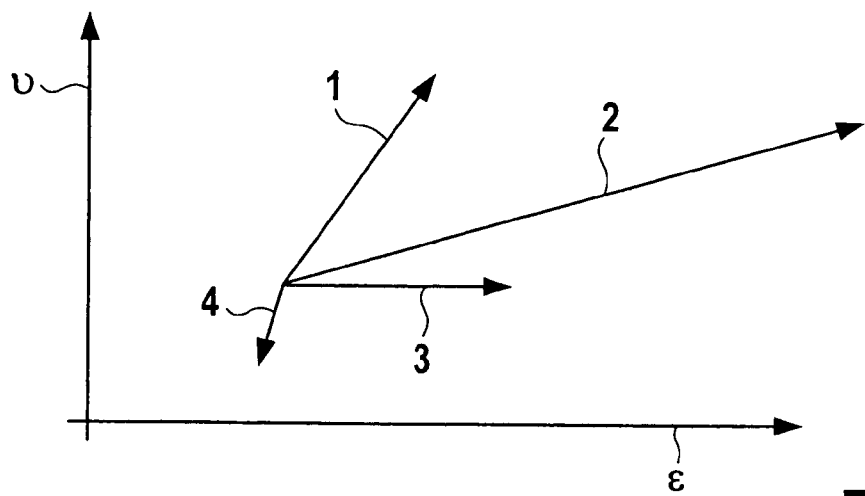
FIG. 1 shows a schematic representation of the influence of contaminants on the physical variables of a motor oil.

In FIG. 1, the influences of oxidation 1, soot concentration 2, water 3 and fuel 4 in an oil are plotted schematically against viscosity v. In addition to the previously described dependency of the viscosity on the contaminants, permittivity $\epsilon$ is likewise dependent on these contaminants, albeit in a different manner. Thus, the addition of water to the motor oil causes an emulsion to form which substantially increases permittivity $\epsilon$, while leaving viscosity v unchanged. In contrast, fuel 4 largely results in a change in viscosity v and leaves permittivity $\epsilon$ unchanged. Soot 2 in the oil and oxidation 1 of the oil both increase viscosity v and permittivity $\epsilon$, oxidation 1 having a less pronounced influence on permittivity $\epsilon$ than soot concentration 2.

Figure 2:
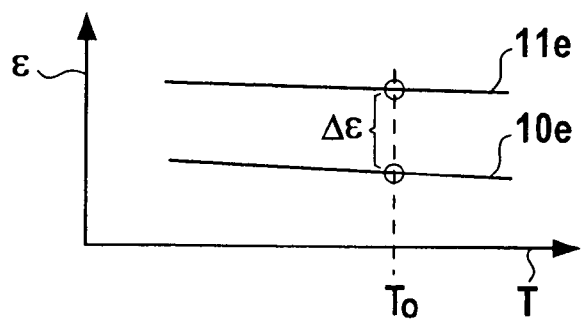
FIGS. 2 through 4 show graphical representations of three steps of an embodiment of the present invention.
Figure 3:
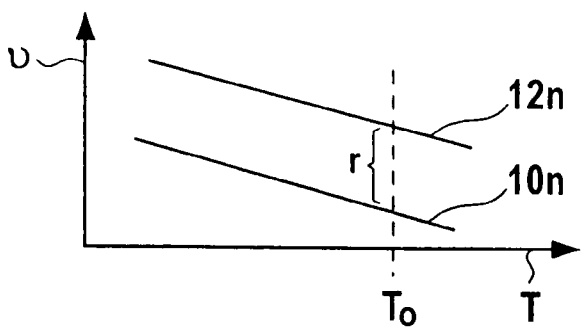
Figure 4:
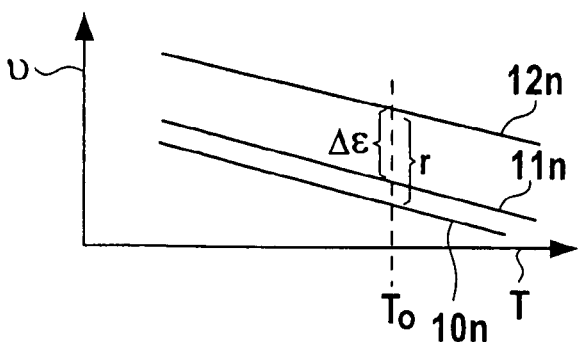

According to one embodiment of the present invention, permittivity $\epsilon$ and viscosity v are used to quantitatively determine the concentration of soot 2 and the quantity of fuel 4 in the used oil. The method largely takes place in three steps and is described with reference to FIGS. 2, 3 and 4. In FIG. 2, the permittivity for used oil 11e and clean oil 10e is plotted over temperature T. Temperature $T_0$ and permittivity $\epsilon$ of contaminated oil 11e are determined in a first method step. Permittivity $\epsilon$ of clean oil at determined temperature $T_0$ is read from precompiled value tables. Resulting difference $\Delta\epsilon$ between permittivity $\epsilon$ of clean oil 10e and contaminated oil 11e is attributable mainly to the contribution of soot 2 and oxidation 1 of the oil. Since the contaminants in the total oil are present only in minute concentrations, it may be assumed that the change in permittivity $\Delta\epsilon$ is proportional to the mass percentage of soot 2 or of oxidized components 1 of the old oil in the total oil. According to the diagram in FIG. 1, an expected change in viscosity r, as shown in FIG. 3, is derived from the determined concentration of soot 2 or oxidized oil 1 from the diagram in FIG. 1. The estimated change in viscosity r is assumed to be proportional to the concentration of soot 2 or oxidized oil 1. FIG. 3 shows a schematic representation of the viscosity for a clean oil 10n in comparison with the viscosity of an oil 12n contaminated with soot 2 for a soot concentration. Viscosity v of contaminated oil 11n is determined in a further step. This generally yields a difference $\Delta v$ between estimated viscosity 12n and detected viscosity 11n of the oil. This difference $\Delta v$ is attributable to concentrations of fuel 4 in the contaminated oil. Assuming that difference $\Delta v$ is proportional to the concentration of fuel 4 in the contaminated oil, this concentration, in turn, may be determined via a predetermined proportionality constant.

The proportionality constants needed to determine the contaminants and estimate the viscosity may be determined ahead of time in laboratory trials and stored in a memory device for the calculations.

In a diesel engine having a soot-particulate filter, a greater increase in the soot concentration of the oil may be a sign that the soot-particulate filter is clogged. The condition of the oil may therefore be used as an indication that the soot-particulate filter needs to be cleaned, e.g., by burn-off or post-injection. Furthermore, a greater increase in fuel concentration in the oil also indicates a malfunction of the soot-particulate filter.

Although the present invention was described with reference to a particularly preferred embodiment, it is not limited thereto. In particular, the sequence of detected physical variables is not rigidly specified. It is therefore also possible to begin by detecting the viscosity and then estimate a permittivity on the basis of the determined viscosity, and to determine the concentration of the fuel and soot on the basis of the difference between the estimated and detected permittivity.

LIST OF REFERENCE NUMERALS

| | |
|---|---|
| 1 | oxidation |
| 2 | soot |
| 3 | water |
| 4 | fuel |
| $\epsilon$ | permittivity |
| 10e | permittivity of clean oil |
| 11e | permittivity of contaminated oil |
| v | viscosity |
| 10n | viscosity of clean oil |
| 11n | viscosity of contaminated oil |
| 12n | estimated viscosity |
| t | time axis |

What is claimed is:

1. A method for a quantitative detection of first and second contaminants in a fluid, comprising:
  detecting first and second physical variables of the fluid, the first physical variable being an electrical variable and the second physical variable being a viscosity of the fluid;
  determining a quantity of the first contaminant on the basis of a difference between the detected first physical variable and a first preset value;
  estimating the second physical variable on the basis of the quantity of the first contaminant; and
  determining a quantity of the second contaminant on the basis of a difference between the detected second physical variable and the estimated second physical variable;
  wherein the electrical variable is one of the permittivity and a specific resistance of the fluid, and
  wherein the first contaminant includes fuel and the second contaminant includes one of soot and oxidized oil.

2. The method according to claim 1, wherein the fluid includes oil.

3. The method according to claim 1, wherein the quantity of the first and second contaminants is determined using a first and a second linear dependency on a difference between the first and second physical variables.

4. The method according to claim 3, wherein the second physical variable is estimated using a third linear dependency on the quantity of the first contaminant.

5. The method according to claim 4, wherein the first physical variable is determined for a fluid without the first and second contaminants as a preset value.

6. The method according to claim 5, further comprising storing the preset value and linear coefficients for the first, second and third linear dependencies for different oil temperatures, and determining a temperature of contaminated oil.

* * * * *